United States Patent [19]

Arora et al.

[11] Patent Number: 5,757,167
[45] Date of Patent: May 26, 1998

[54] VOLTAGE REGULATOR

[75] Inventors: Suneel Arora, Minneapolis; David W. Kelly, Lino Lakes, both of Minn.

[73] Assignee: Cardiac Pacemakers, Inc., St. Paul, Minn.

[21] Appl. No.: 678,965

[22] Filed: Jul. 12, 1996

[51] Int. Cl.[6] .................................................. G05F 1/613
[52] U.S. Cl. ............................................................ 323/224
[58] Field of Search .................................. 323/220, 223, 323/224, 226, 266, 270, 273, 280, 911; 607/33, 61; 307/45, 49, 61, 77

[56] References Cited

U.S. PATENT DOCUMENTS

| | | | |
|---|---|---|---|
| 4,134,408 | 1/1979 | Brownlee et al. | 128/419 PS |
| 4,408,607 | 10/1983 | Maurer | 128/419 R |
| 4,672,973 | 6/1987 | Hofke | 128/665 |
| 4,868,908 | 9/1989 | Pless et al. | 323/267 |
| 5,424,683 | 6/1995 | Takahashi | 330/255 |
| 5,528,087 | 6/1996 | Sibata et al. | 323/224 |

OTHER PUBLICATIONS

J. G. Ryan, et al., "A Four Chip Implantable Defibrillator/Pacemaker Chipset", *Proceedings of the IEEE 1989 Custom Integrated Circuits Conference*, San Diego, CA, pp. 7.6.1–7.6.4, (May 15–18, 1989).

*Primary Examiner*—Matthew V. Nguyen
*Attorney, Agent, or Firm*—Schwegman, Lundberg, Woessner & Kluth, P.A.

[57] ABSTRACT

A voltage regulator in a battery powered device, such as an implantable cardiac defibrillator, provides regulated output voltage for other circuits. When large currents are drawn from the battery, such as during charging of defibrillation output capacitors, switches decouple the regulator from receiving power from the battery and couple the regulator to receive power from a stable boost output voltage generated by a boost converter. The regulator provides a stable regulated output voltage less noisy than the boost output voltage. Controlled switch conductances in the regulator provide operation over a wide range of output load currents.

25 Claims, 9 Drawing Sheets

VOLTAGE REGULATOR

THE FIELD OF THE INVENTION

This invention relates to semiconductor power supply circuits, and more particularly to a voltage regulation system capable of use in a battery powered implantable medical device.

BACKGROUND OF THE INVENTION

In battery operated devices such as implantable cardiac pacemakers and defibrillators an internal resistance of the battery imposes certain limitations on the device. One such limitation arises as large currents drawn from the battery decrease the terminal voltage of the battery. If the drawn current is sufficiently large, the battery terminal voltage will decrease below the voltage level required to operate devices powered from the battery.

This problem is particularly prevalent in implantable cardiac defibrillators which typically draw large currents from the battery for short periods of time during the charging of defibrillation output capacitors. This large drawn current causes a significant drop in the battery terminal voltage. Thus, there is a need in the art to provide a stable voltage from which to operate battery powered devices, such as implantable cardiac pacemakers and defibrillators, in spite of appreciable drop in the battery terminal voltage such as occurs during the charging of the defibrillation output capacitors in cardiac defibrillation.

SUMMARY OF THE INVENTION

The present invention provides a regulator for generating a regulated output voltage. The regulator includes an amplifier circuit having a first amplifier power terminal. A first switch receives a first power supply and couples the first power supply to the first amplifier power terminal. A second switch receives a second power supply and couples the second power supply to the first amplifier power terminal. A control circuit controls the first and second switches such that the amplifier is capable of receiving power from both of the first and second power supplies.

In one embodiment of the present invention, the amplifier is configured in a noninverting feedback arrangement. In this embodiment, a first resistor is coupled between an inverting amplifier input terminal and an amplifier output terminal. A second resistor is coupled between the inverting amplifier input terminal and a ground terminal. A reference voltage is coupled to a noninverting amplifier input terminal.

In one embodiment, the amplifier also comprises a second amplifier power terminal. A third switch couples the second amplifier power terminal to the first power supply. A fourth switch couples the second amplifier power terminal to the second power supply. The control circuit controls each of the first, second, third, and fourth switches. In one embodiment, the control circuit controls the conductances of the third and fourth switches as a function of a load current delivered at the amplifier output terminal. Controlling the conductances of the third and fourth switches as a function of the load current delivered at the amplifier output terminal improves the frequency response of the amplifier circuit.

In one embodiment, the first power supply is provided by a battery. A boost converter receives the first power supply and generates the second power supply. In one form of this embodiment, the present invention operates as part of a cardiac rhythm management device such as an implantable defibrillator. During charging of defibrillation output capacitors, large currents are drawn from the battery, causing its terminal voltage to drop. During such periods, the regulator is isolated from the battery and coupled to the second power supply provided by the boost converter. Since the second power supply remains stable during charging of defibrillation output capacitors, the regulated output voltage also remains stable.

BRIEF DESCRIPTION OF THE DRAWINGS

In the drawings, like numerals describe like components throughout the several views.

DESCRIPTION OF THE PREFERRED EMBODIMENTS

In the following detailed description of the preferred embodiments, reference is made to the accompanying drawings which form a part hereof, and in which is shown by way of illustration specific embodiments in which the invention may be practiced. It is to be understood that other embodiments may be utilized and structural or logical changes may be made without departing from the scope of the present invention. The following detailed description, therefore, is not to be taken in a limiting sense, and the scope of the present invention is defined by the appended claims and their equivalents.

Figure 1:
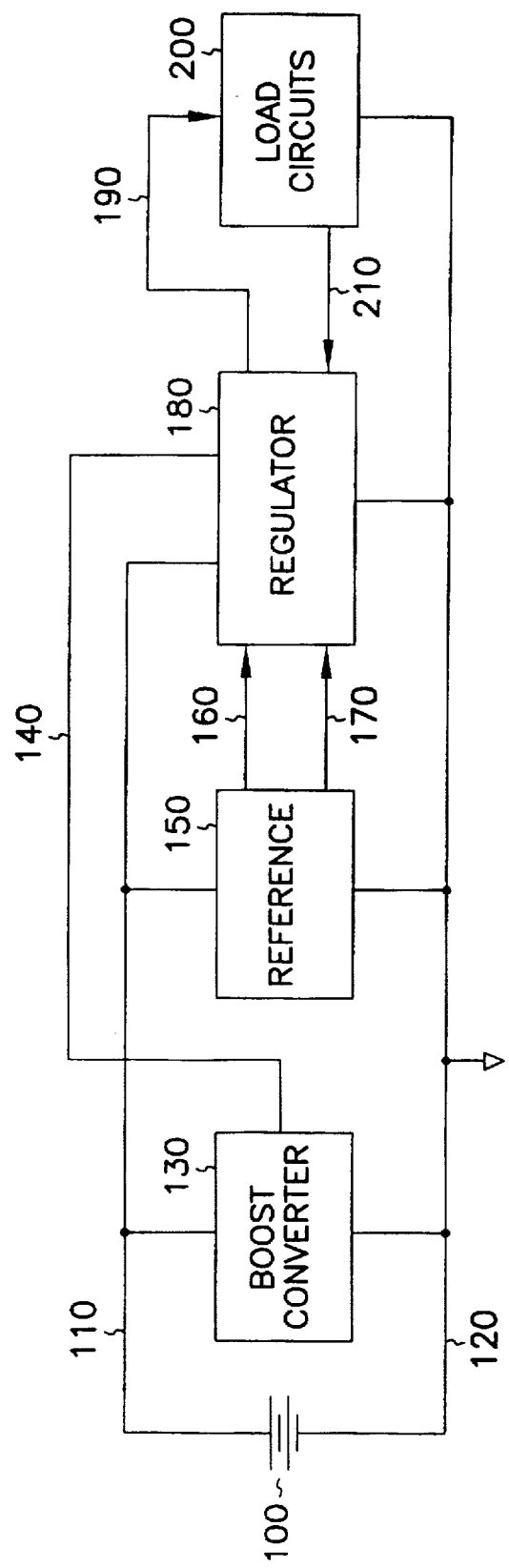
FIG. 1 is a system level block diagram illustrating the invention and its environment, including: a battery; boost converter; reference circuit; and load circuits.

The present invention provides a stable regulated voltage from which to operate battery powered integrated circuits in spite of appreciable drop in battery terminal voltage. FIG. 1 is a system level block diagram of one embodiment of a voltage regulator according to the present invention and its environment. FIG. 1 illustrates a battery 100 having a first terminal generating a first power supply at node 110 and having a second terminal coupled to ground node 120. A boost converter 130 is coupled to first power supply node 110 and ground node 120. Boost converter 130 provides a second power supply voltage at node 140. A reference circuit 150 is coupled to first power supply node 110 and ground node 120. Reference circuit 150 provides a reference voltage at node 160 and a reference current at node 170. A regulator 180 is coupled to each of the first and second power supplies at nodes 110 and 140 and is coupled to ground node 120.

Regulator 180 is also coupled to reference circuit 150, receiving the reference voltage at node 160 and the reference current at node 170. Regulator 180 provides a regulated output voltage at node 190 to load circuits 200. Load circuits 200 comprise circuits desired by the designer of the battery powered system to be powered from the regulated output voltage at node 190. Load circuits 200 also provide a digital supply toggling signal at node 210 coupled to and received by regulator 180. Regulator 180 arbitrates between first and second power supplies at nodes 110 and 140 based upon a binary logic value of the supply toggling signal at node 210.

Figure 2:
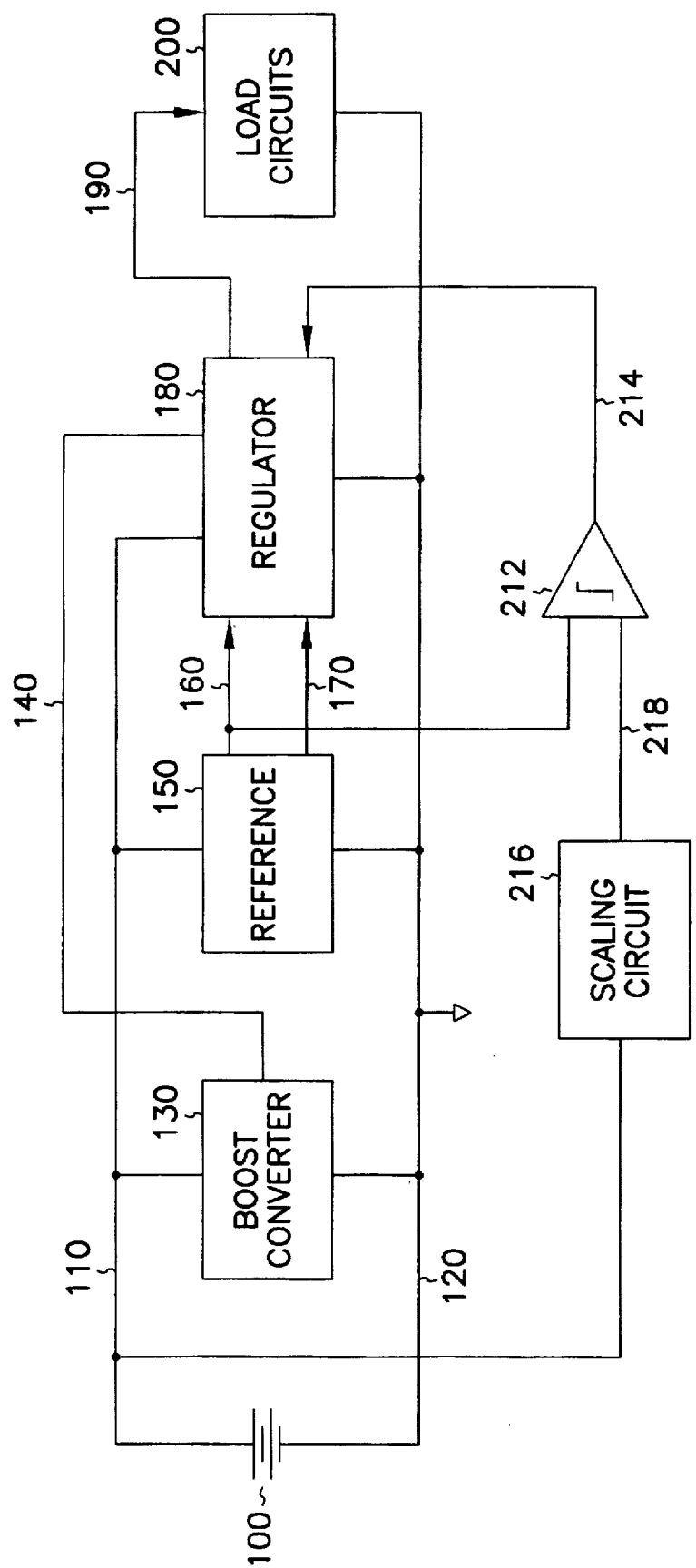
FIG. 2 is a system level block diagram illustrating an alternate embodiment of the invention and its environment, including: a battery; boost converter; reference circuit; load circuits; scaling circuit; and comparator.

FIG. 2 is a system level block diagram of an alternate embodiment and environment of a voltage regulator according to the present invention. The operation and environment of the voltage regulator of FIG. 2 is similar to that of the voltage regulator of FIG. 1; only the main distinguishing features are discussed below in reference to FIG. 2. In FIG. 2, a comparator 212 provides a digital supply toggling signal at node 214 coupled to and received by regulator 180. Scaling circuit 216 receives the first power supply at node 110 and provides an appropriately scaled output voltage at node 218. Comparator 212 compares the reference voltage at node 160 to the scaled voltage at node 218. While the first power supply voltage at node 110 remains above a predetermined level defined by scaling circuit 216 and the reference voltage at node 160, regulator 180 receives power from the first power supply for generating the regulated output voltage at node 190. When the first power supply voltage at node 110 falls below a predetermined level, regulator 180 receives power from a second power supply for generating the regulated output voltage at node 190.

Figure 3:
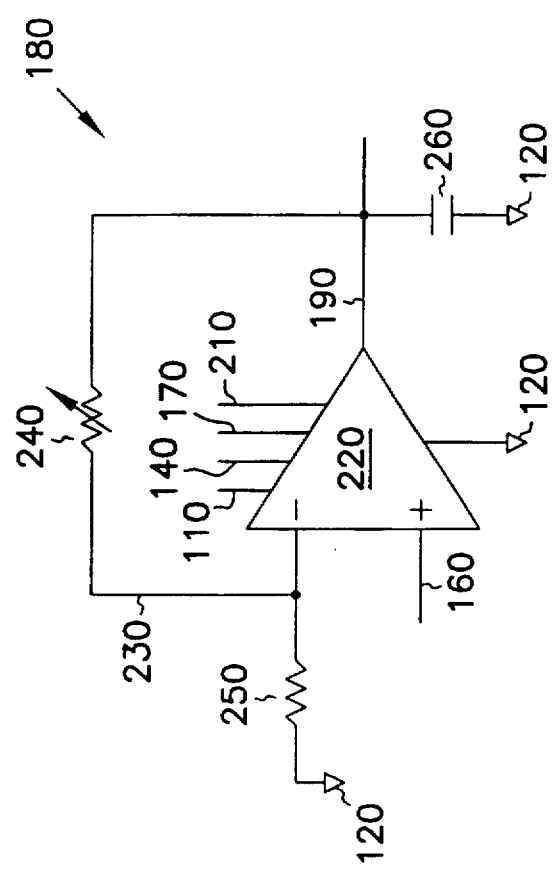
FIG. 3 is a schematic diagram illustrating the regulator of FIG. 1 in more detail, including a regulator subcircuit.

FIG. 3 is a schematic diagram illustrating regulator 180 in more detail. Regulator 180 comprises a regulator subcircuit 220 coupled to and receiving the reference voltage at node 160. Regulator subcircuit 220 is also coupled to an inverting amplifier input node 230. Regulator subcircuit 220 is coupled to and receives first and second power supplies at nodes 110 and 140, ground node 120, the reference current at node 170, and the supply toggling signal at node 210. Regulator subcircuit 220 comprises an output terminal providing the regulated output voltage at node 190. Regulator 180 also comprises a first resistor 240 coupled between inverting amplifier input node 230 and regulated output voltage node 190. Regulator 180 also comprises a second resistor 250 coupled between the inverting amplifier input node 230 and ground node 120. Regulator 180 also comprises a filter capacitor 260 having a first terminal coupled to the regulated output voltage node 190 and a second terminal coupled to ground node 120. Filter capacitor 260 stabilizes the output voltage provided by regulator subcircuit 220 at regulated output voltage node 190. Regulator subcircuit 220 and first and second resistors 240 and 250 function as an amplifier in a noninverting feedback configuration. Other feedback configurations could also be used to meet particular design requirements, including: a voltage follower; an inverting amplifier; a summing amplifier; a difference amplifier feedback; and an integrating amplifier.

Figure 4:
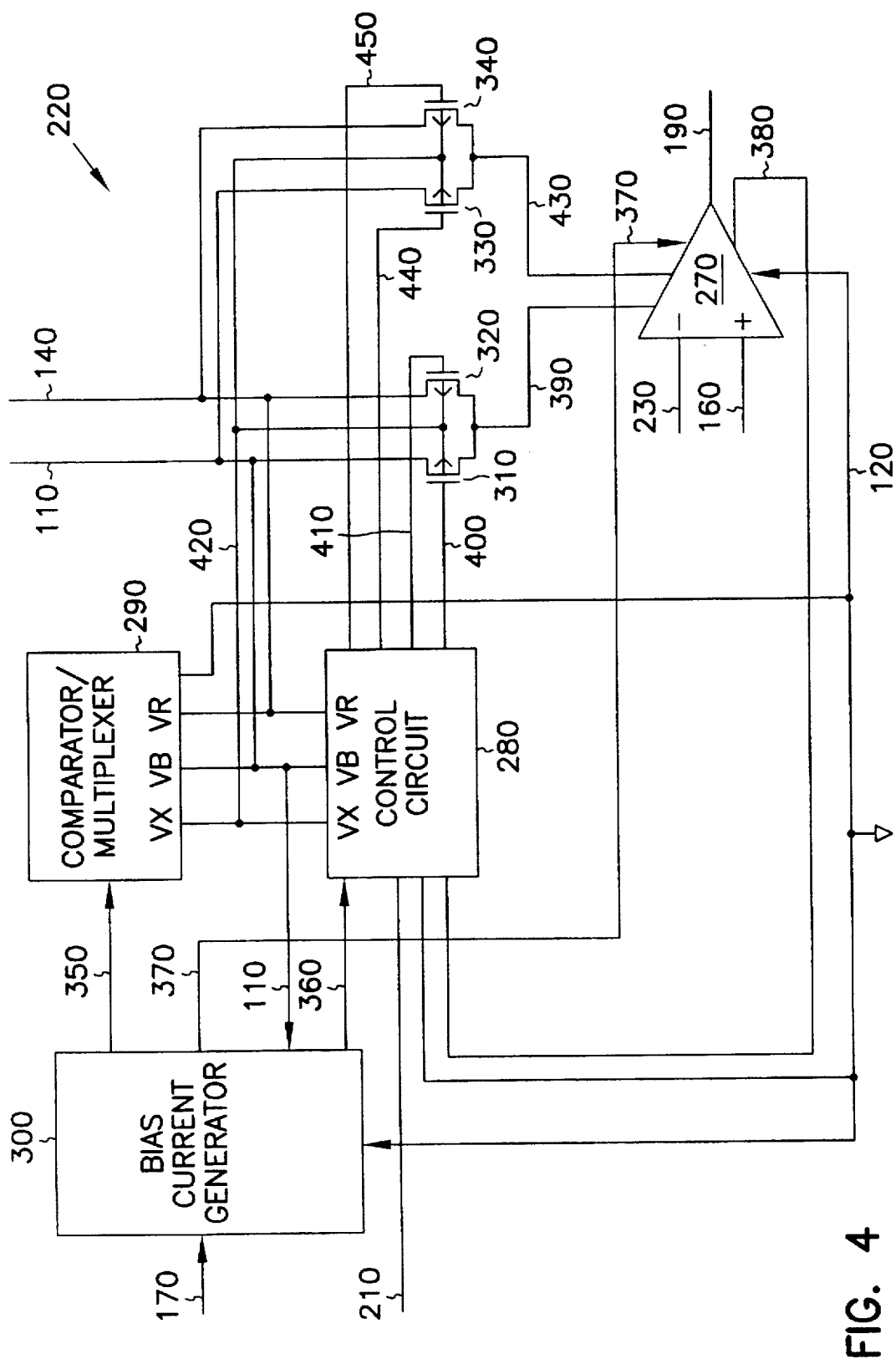
FIG. 4 is a schematic diagram illustrating the regulator subcircuit of FIG. 3 in more detail, including: an amplifier; a comparator/multiplexer; and a control circuit.

FIG. 4 is a schematic diagram illustrating regulator subcircuit 220 in more detail. Regulator subcircuit 220 comprises: amplifier 270; control circuit 280; comparator/multiplexer 290; bias current generator 300; first switch 310; second switch 320; third switch 330; and fourth switch 340.

As illustrated in FIG. 4, bias current generator 300 receives current from the reference current at node 170, first power supply node 110, and ground node 120. Bias current generator 300 uses MOS FET current mirrors to generate independent bias currents coupled and delivered to comparator/multiplexer 290, control circuit 280, and amplifier 270 at nodes 350, 360, and 370 respectively.

Amplifier 270 comprises a noninverting amplifier input terminal coupled to and receiving the reference voltage at node 160, an inverting amplifier input terminal coupled to and receiving inverting amplifier input node 230, an amplifier bias current terminal coupled to and receiving a bias current from bias current generator 300 at node 370, and a ground terminal coupled to ground node 120. Amplifier 270 also comprises an amplifier output terminal coupled to regulated output voltage node 190 and a sense current output provided to control circuit 280 at node 380.

Amplifier 270 also comprises a first amplifier power terminal at node 390 coupled to each of first and second power supply nodes 110 and 140 through first and second switches 310 and 320. First and second switches 310 and 320 are p-channel metal-oxide-semiconductor (PMOS) field-effect transistors (FETs), each coupled at their respective drain terminals to the first amplifier power terminal at node 390. First switch 310 receives from control circuit 280 a control signal at its gate terminal coupled to node 400. Second switch 320 receives from control circuit 280 a control signal at its gate terminal coupled to node 410. Both of first and second switches 310 and 320 have their respective body terminals coupled to and receiving a most positive supply signal at node 420. First switch 310 receives first power supply node 110 at its source terminal. Second switch 320 receives second power supply node 140 at its source terminal. Control circuit 280 provides control signals to each of first and second switches 310 and 320 coupling one of first and second power supplies nodes 110 and 140 to the first amplifier power terminal at node 390.

Amplifier 270 also comprises a second amplifier power terminal at node 430 coupled to each of first and second power supply nodes 110 and 140 through third and fourth switches 330 and 340. Third and fourth switches 330 and 340 are p-channel metal-oxide-semiconductor (PMOS) field-effect transistors (FETs). Each of third and fourth switches 330 and 340 is coupled at its drain terminal to the second amplifier power terminal at node 430. Third switch 330 receives from control circuit 280 a control signal at its gate terminal coupled to node 440. Fourth switch 340 receives from control circuit 280 a control signal at its gate terminal coupled to node. Both of third and fourth switches 330 and 340 are coupled to most positive supply node 420 at their respective body terminals. Third switch 330 receives first power supply node 110 at its source terminal. Fourth switch 320 receives second power supply node 140 at its source terminal. Control circuit 280 provides control signals to each of third and fourth switches 330 and 340 coupling one of first and second power supply nodes 110 and 140 to second amplifier power terminal at node 430. Third and fourth switches 330 and 340 have controlled conductances based on a function of the load current delivered at the amplifier output terminal coupled to regulated output voltage node 190, as discussed in detail below.

Comparator/multiplexer 290 receives the bias current at node 350 from bias current generator 300, first and second power supplies nodes 110 and 140 respectively, and ground node 120. Comparator/multiplexer 290 compares the voltages at first and second power supply nodes 110 and 140 respectively to determine which is more positive. Comparator/multiplexer 290 couples this more positive of first and second power supplies nodes 110 and 140 respectively to the most positive supply node 420. Most positive supply node 420 is provided to other circuits, including control circuit 280 and the body terminal of each of first, second, third, and fourth switches 310, 320, 330, 340 respectively.

Control circuit 280 receives the bias current at node 360 from bias current generator 300, first and second power supply nodes 110 and 140 respectively, ground node 120, most positive supply node 420, the sense current at node 380, and the supply toggling signal at node 210. Control circuit 280 provides control signals at nodes 400 and 410 to first and second switches 310 and 320 respectively for coupling amplifier 270 to one of first and second power supply nodes 110 and 140 respectively. Control circuit 280 also provides control signals at nodes 440 and 450 to third and fourth switches 330 and 340 respectively for coupling amplifier 270 to one of first and second power supply nodes 110 and 140 respectively. The control signals at nodes 440 and 450 are a function of the load current delivered by amplifier 270 at its output terminal coupled to regulated output voltage node 190, where this load current is replicated and fed back to control circuit 280 as the sense current at node 380.

Figure 5:
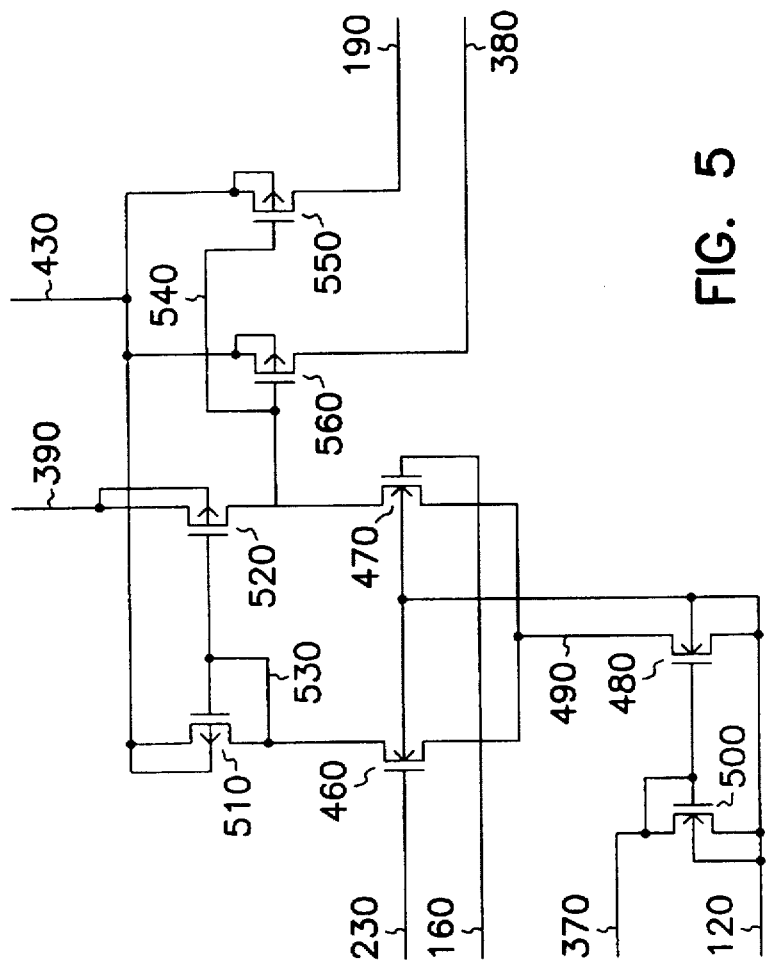
FIG. 5 is a schematic diagram illustrating the amplifier of FIG. 4 in more detail.

FIG. 5 is a schematic diagram illustrating amplifier 270 in more detail. Amplifier 270 includes a source-coupled differential pair of input FETs 460 and 470. Input FETs 460 and 470 are typically n-channel metal-oxide-semiconductor (NMOS) FETs. A gate terminal of input FET 460 is coupled to and receives inverting amplifier input node 230. A gate terminal of input FET 470 is coupled to and receives reference voltage node 160. Input FETs 460 and 470 are coupled to each other at their source terminals and are also coupled to a drain terminal of NMOS current mirror FET 480 at node 490. Current mirror FET 480 has its source and body terminals coupled to ground node 120. Current mirror FET 480 has its gate terminal coupled to the gate terminal of a diode-connected current mirror FET 500. Current mirror FET 500 has its source and body terminals coupled to ground node 120. Current mirror FET 500 receives at its coupled gate and drain terminals the bias current at node 370, and generates a voltage in response thereto at node 370. Current mirror FET 480 receives the voltage at node 370. In response thereto, current mirror FET 480 provides to source-coupled input FETs 460 and 470 a scaled version of the bias current received by diode-connected current mirror FET 500 at node 370.

Input FETs 460 and 470 are coupled at their respective drain terminals to drain terminals of PMOS current mirror load FETs 510 and 520. Current mirror load FET 510 is diode-connected with its gate and drain terminals coupled to the drain terminal of input FET 460 and to the gate terminal of current mirror load FET 520 at node 530. Diode-connected current mirror load FET 510 has its source and body terminals coupled to second amplifier power terminal node 430. Current mirror load FET 520 has its source and body terminals coupled to first amplifier power terminal node 390. Current mirror load FET 520 has its drain terminal coupled at node 540 to the drain terminal of input FET 470 and to the gate terminals of PMOS output transconductance FET 540 and PMOS current monitor FET 550.

Output transconductance FET 550 forms a second stage of amplifier 270, the first stage of amplifier 270 comprising input FETs 460 and 470 and current mirror load FETs 510 and 520. Output transconductance FET 550 has its source and body terminals coupled to the second amplifier power terminal at node 430 and its drain terminal provides an output voltage and load current at the amplifier output terminal coupled to regulated output voltage node 190.

Current monitor FET 560 is configured in parallel with output transconductance FET 550, except at a drain terminal of current monitor FET 550, which is coupled to control circuit 280 at sense current node 380. The source and body terminals of current monitor FET 560 are each coupled to the second amplifier power terminal at node 430. The physical geometry of current monitor FET 560 includes a width/length aspect ratio which is scaled downward from that of output transconductance FET 550. A fraction of the load current delivered by output transconductance FET 550 at the amplifier output terminal coupled to regulated output voltage node 190 is replicated by current monitor FET 560 and provided to control circuit 280 at sense current node 380.

First amplifier power terminal node 390 is coupled to one of the first and second power supply nodes 110 and 140 by one of first and second switches 310 and 320. Second amplifier power terminal at node 430 is coupled to one of the first and second power supply nodes 110 and 140 by one of third and fourth switches 330 and 340. Control circuit 280 controls first, second, third, and fourth switches 310, 320, 330, and 340 respectively, to ensure that each of first and second amplifier power terminals nodes 390 and 430 are not simultaneously coupled to both of first and second power supply nodes 110 and 140. Control circuit 280 also controls the conductances of third and fourth switches 330 and 340 based on the fraction of the load current generated by current monitor FET 560 and provided to control circuit 280 at sense current node 380. By controlling the conductances of third and fourth switches 330 and 340 in this manner, certain amplifier characteristics such as stability are enhanced over a wide range of load currents delivered at amplifier output terminal coupled to the regulated output voltage node 190, as explained in detail below.

The open loop frequency response of amplifier 270 is illustrated in Equation 1.

$$\frac{v_{190}}{v_{160}} = \frac{v_{540}}{v_{160}} \times \frac{v_{190}}{v_{540}} \quad (1)$$

In Equation 1, $v_{540}/v_{160}$ is a first stage voltage transfer function from reference voltage node 160 to node 540; and $v_{190}/v_{540}$ is a second stage voltage transfer function from node 540 to the amplifier output terminal at regulated output voltage node 190.

The first stage voltage transfer function corresponds primarily to the first stage of amplifier 270, comprising input FETs 460 and 470 and current mirror load FETs 510 and 520, and is approximated by Equation 2.

$$\frac{v_{540}}{v_{160}} = \frac{gm_{460}}{gds_{520} + gds_{470} + j\omega Cg_{550} + \frac{gm_{550}gm_{520}}{gds_{330/340}}} \quad (2)$$

In Equation 2, $gm_{460}$ is a transconductance of input FET 460; $gds_{520}$ is an output conductance of current mirror load FET 520; $j\omega$ is complex frequency; $Cg_{550}$ is a lumped capacitance at node 540 dominated by the gate capacitance of output transconductance FET 550; $gm_{550}$ is a transconductance of output transconductance FET 550; $gm_{520}$ is a transconductance of current mirror load FET 520; $gds_{330/340}$ is an output conductance of the one of third and fourth switches 330 and 340 coupling the second amplifier power terminal at node 430 to one of first and second power supply nodes 110 and 140. The first stage voltage transfer function of Equation 2 forms a high frequency pole in the frequency response of amplifier 270.

The second stage voltage transfer function corresponds primarily to the second stage of amplifier 270, comprising output transconductance FET 550, and is approximated in Equation 3.

$$\frac{v_{190}}{v_{340}} = \frac{gm_{550}}{gds_{550} + j\omega C_{260} + g_{LOAD}} \quad (3)$$

In Equation 3, $gm_{550}$ is the transconductance of output transconductance FET 550; $gds_{550}$ is an output conductance of output transconductance FET 550; $j\omega$ is complex frequency; $C_{260}$ is the capacitance of filter capacitor 260 of FIG. 3 coupled between amplifier output node 190 and ground node 120; and $g_{LOAD}$ is a load conductance of load circuits 200 of FIG. 1. The second stage voltage transfer function of Equation 3 forms a low frequency pole in the frequency response of amplifier 270.

Amplifier 270 is capable of stable operation over a wide range of load currents delivered at amplifier output terminal coupled to regulated output voltage node 190. Since small signal parameters such as transconductance and output conductance vary with bias current, the frequency response of typical two stage amplifiers may vary significantly with load current. The last term in the denominator of Equation 2 is a gain degeneration term corresponding to the controlled conductance between second amplifier power terminal 430 and one of first and second power supplies 110 and 140. Since $gm_{550}$ is proportional to load current delivered at amplifier output terminal 190, a large dc load current reduces the gain of the first stage voltage transfer function of Equation 2, pushes the first stage pole to a higher frequency, and improves the stability of amplifier 270.

Though the above described gain degeneration improves the stability of amplifier 270 for large load currents, it is difficult to provide sufficient gain degeneration over a wide range of load currents such as, for example, over the range between 10 microamperes and 3 milliamperes. For this reason, the $gds_{330/340}$ term in Equation 2 is adjusted by control circuit 280 as a function of the load current as replicated by current monitor FET 560 and delivered to control circuit 280 at sense current node 380, as described in detail below.

Figure 6:
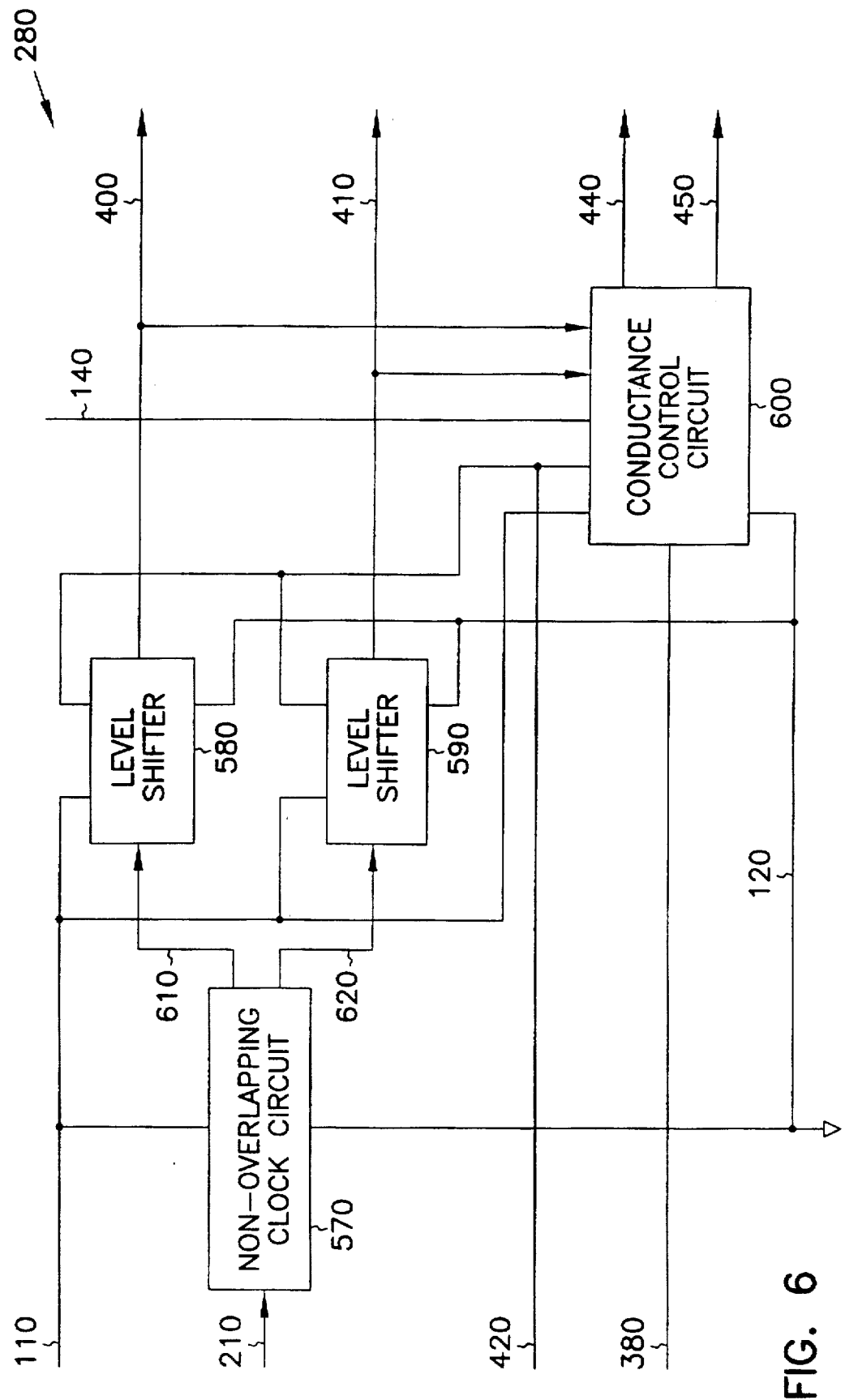
FIG. 6 is a schematic diagram illustrating the control circuit of FIG. 4 in more detail, including a conductance control circuit.

FIG. 6 is a schematic block diagram illustrating control circuit 280 in more detail. Control circuit 280 comprises non-overlapping clock circuit 570, first and second level shifters 580 and 590 respectively, and conductance control circuit 600. Non-overlapping clock circuit 570 receives first power supply node 110 and ground node 120. Non-overlapping clock circuit 570 also receives the supply toggling signal at node 210 from load circuits 200. During periods when voltage drop in the voltage at first power supply node 110 is expected due to large currents drawn from battery 100, load circuits 200 change the binary logic value of supply toggling signal at node 210 from a binary logic low value to a binary logic high value. In response, control circuit 280 electrically isolates amplifier 270 from first power supply node 110 and electrically couples amplifier 270 to second power supply node 140.

In one embodiment, voltage drop at first power supply node 110 is due to use of the present invention in an implantable cardiac defibrillator where first battery 100 generates the voltage at first power supply node 110. The implantable cardiac defibrillator draws particularly large currents from first power supply node 110 for short periods of time while defibrillation output capacitors are charged. Since the voltage at first power supply node 110 is generated by battery 100 having a finite internal resistance, such large currents drawn from first power supply node 110 impose significant voltage drop in voltage at first power supply node 110. The voltage at second power supply node 140 remains stable because it is generated from boost converter 130, as described below.

Non-overlapping clock circuit 570 generates first and second control voltages 610 and 620 respectively based on the binary logic value of the supply toggling signal at node 210, as illustrated in Table 1.

TABLE 1

| Supply Toggling Signal At Node 210 | First Control Voltage At Node 610 | Second Control Voltage At Node 620 |
|---|---|---|
| 0 | 0 | 1 |
| 1 | 1 | 0 |

Non-overlapping clock circuit 570 ensures that first and second control voltages 610 and 620 are not simultaneously at a binary logic low value even during and after transitions of the supply toggling signal at node 210 from a binary logic low to a binary logic high and vice versa.

Level shifters 580 and 590 respectively receive as inputs the first and second control voltages at nodes 610 and 620 from non-overlapping clock circuit 570. Level shifters 580 and 590 also each receive first and second power supply nodes 110 and 140, most positive supply node 420, and ground node 120. Level shifters 580 and 590 translate the logic levels of the first and second control voltages at nodes 610 and 620 to corresponding level shifted first and second control voltages output at nodes 400 and 410 respectively. The level shifted first and second control voltages at nodes 400 and 410 have a binary logic high voltage approximately equal to the voltage at most positive supply node 420 and have a binary logic low voltage approximately equal to the voltage at ground node 120. The level shifted first and second control voltages at nodes 400 and 410 are coupled to gate terminals of PMOS FET first and second switches 310 and 320 respectively, and are also coupled as inputs to conductance control circuit 600.

Conductance control circuit 600 receives as inputs the level shifted first and second control voltages at nodes 400 and 410, and also receives the sensed current at node 380. Conductance control circuit 600 also receives first and second power supply nodes 110 and 140 respectively, most positive supply node 420, and ground node 120. Conductance control circuit 600 outputs third and fourth level shifted control signals at nodes 440 and 450. Third level shifted control signal at node 440 is coupled to the gate terminal of third switch 330. Fourth level shifted control signal at node 450 is coupled to the gate terminal of fourth switch 340. Third and fourth level shifted control signals at nodes 440 and 450 each have a binary logic high voltage approximately equal to most positive supply voltage node 420. Third and fourth level shifted control signals at nodes 440 and 450 have a binary logic low voltage which varies depending on the load current delivered at amplifier output terminal coupled to regulated output voltage node 190, where this load current is replicated by current monitor FET 560 at sense current node 380.

Figure 7:
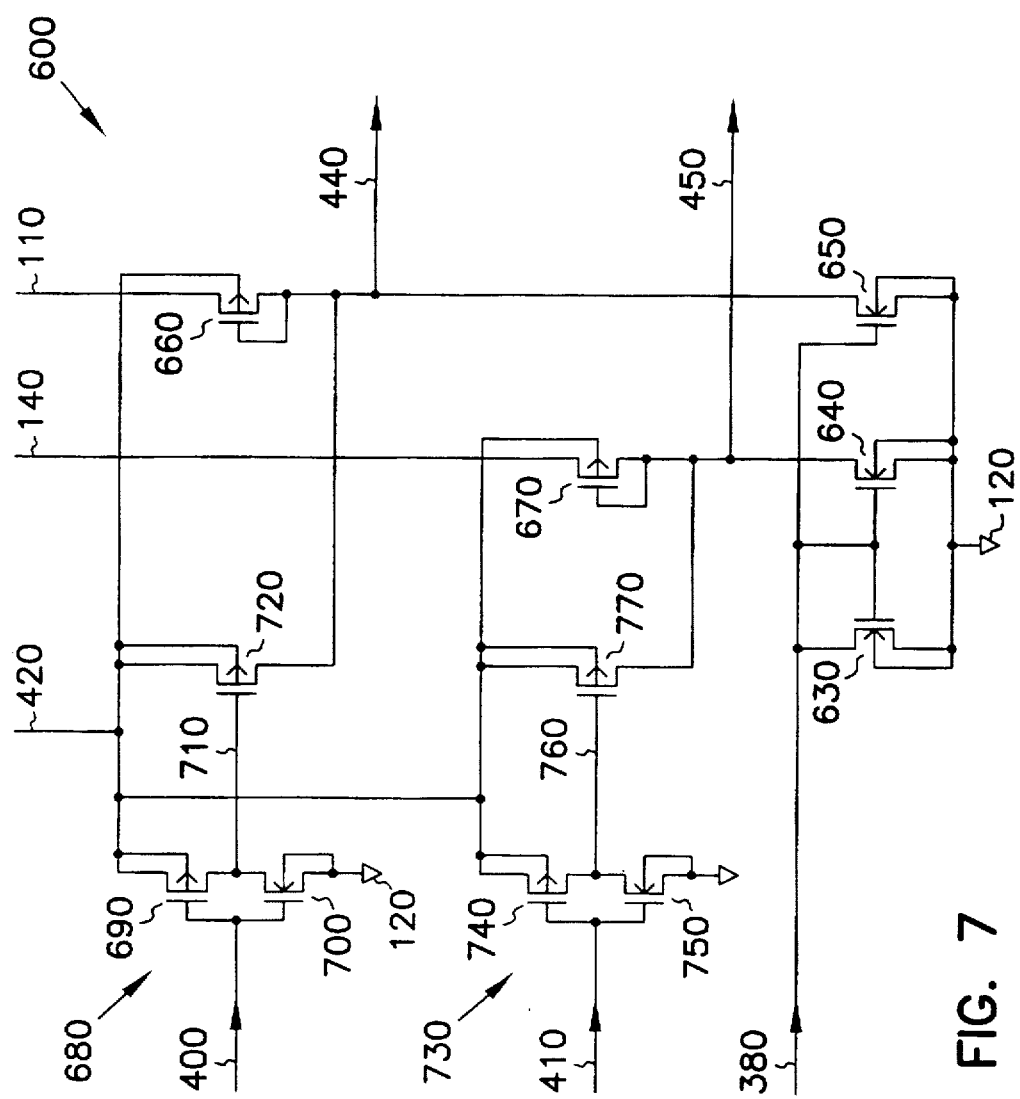
FIG. 7 is a schematic diagram illustrating the conductance control circuit of FIG. 6 in more detail.

FIG. 7 is a schematic diagram illustrating conductance control circuit 600 in more detail. Sense current node 380 is coupled to and received by drain and gate terminals of diode-connected NMOS FET 630 and converted to a voltage at node 380. Source and body terminals of diode-connected NMOS FET 630 are each coupled to ground node 120. The voltage at sense current node 380 is coupled to and received by gate terminals of each of NMOS current mirror FETs 640 and 650. In response, the current received at sense current node 380 is replicated at the drain terminals of current mirror FETs 640 and 650. The drain terminals of current mirror FETs 640 and 650 are coupled to third and fourth level shifted control signal nodes 440 and 450 respectively.

The current at the drain terminal of current mirror FET 650 is coupled to each of the gate and drain terminals of diode-connected PMOS load FET 660 at third level shifted control signal node 440. The current at the drain terminal of current mirror FET 640 is coupled to each of the gate and drain terminals of diode-connected PMOS load FET 670 at fourth level shifted control signal node 450. Load FET 660 has its source and body terminals coupled to first power supply 110. Load FET 670 has its source and body terminals coupled to second power supply 140. Thus, the voltage at third level shifted control signal node 440 is referenced to and translated downward from the first power supply node 110 as a function of current received at sense current node 380. Similarly, the voltage at fourth level shifted control signal node 450 is referenced to and translated downward from the second power supply node 140 as a function of current received at sense current node 380. The current received at sense current node 380 is in turn a function of the load current delivered at the amplifier output coupled to regulated output voltage node 190.

Thus, the third and fourth level shifted control signals at nodes 440 and 450 provide to respective third and fourth switches 330 and 340 gate drive voltages which are a function of the load current delivered to the amplifier output coupled to regulated output voltage node 190. In turn, these gate drive voltages at nodes 440 and 450 produce conductances in third and fourth switches 330 and 340 which are also a function of the load current delivered at the amplifier output at node 190. This improves the frequency response of amplifier 270 as described above.

Inverter 680 comprises PMOS FET 690 and NMOS FET 700. Inverter 680 receives first level shifted control signal at node 400. The first level shifted control signal at node 400 has a binary high logic level voltage approximately equal to the voltage at most positive supply node 420 and a binary low logic level voltage approximately equal to the voltage at ground node 120. Inverted values of these logic levels are output at node 710 coupled to a gate terminal of a PMOS first pullup switch 720. First pullup switch 720 has its source and body terminals coupled to most positive supply node 420. First pullup switch 720 has its drain terminal coupled to third level shifted control signal node 440. When the first level shifted control signal at node 400 is at its binary high logic level, the gate terminal at node 710 of first pullup switch 720 is discharged to the voltage at ground node 120 through FET 700. In this state, first pullup switch 720 provides a binary logic high voltage approximately equal to the voltage of most positive supply node 420 to the third level shifted control signal at node 440. When the first level shifted control signal at node 400 is at its binary low logic level, the gate terminal at node 710 of first pullup switch 720 is charged to the voltage of most positive supply node 420 through FET 690. In this state, first pullup switch 720 is off, and load FET 660 provides to the third level shifted control signal at node 440 the binary logic low voltage which is a function of the load current at the amplifier output terminal coupled to regulated output voltage node 190.

Inverter 730 comprises PMOS FET 740 and NMOS FET 750. Inverter 730 receives second level shifted control signal at node 410. The second level shifted control signal at node 410 has a binary high logic level voltage approximately equal to the voltage at most positive supply node 420 and a binary low logic level voltage approximately equal to the voltage at ground node 120. These logic levels are output at node 760 coupled to the gate terminal of PMOS second pullup switch 770. Second pullup switch 770 has its source and body terminals coupled to most positive supply node 420. Second pullup switch 770 has its drain terminal coupled to fourth level shifted control signal node 440. When the second level shifted control signal at node 410 is at its binary high logic level, the gate terminal at node 760 of second pullup switch 770 is discharged to the voltage at ground node 120 through FET 750. In this state, second pullup switch 770 provides a binary logic high voltage approximately equal to the voltage of most positive supply node 420 to the fourth level shifted control signal. When the second level shifted control signal at node 410 is at its binary low logic level, the gate terminal at node 760 of second pullup switch 770 is charged to the voltage of most positive supply node 420 through FET 740. In this state, second pullup switch 770 is off, and load FET 670 provides to the fourth level shifted control signal at node 450 a binary logic low voltage which is a function of the load current at the amplifier output terminal coupled to regulated output voltage node 190.

As described above, non-overlapping clock circuit 570 prevents third and fourth level shifted control signals at nodes 440 and 450 respectively from simultaneously being at their binary logic low voltage levels. As the load current delivered by the amplifier output at regulated output voltage node 190 is increased, one of the third and fourth level shifted control signal voltages at nodes 440 and 450 is decreased, thereby increasing the conductance $gds_{330/340}$ of one of third and fourth switches 330 and 340. This improves the frequency response of amplifier 270 as described above.

Figure 8:
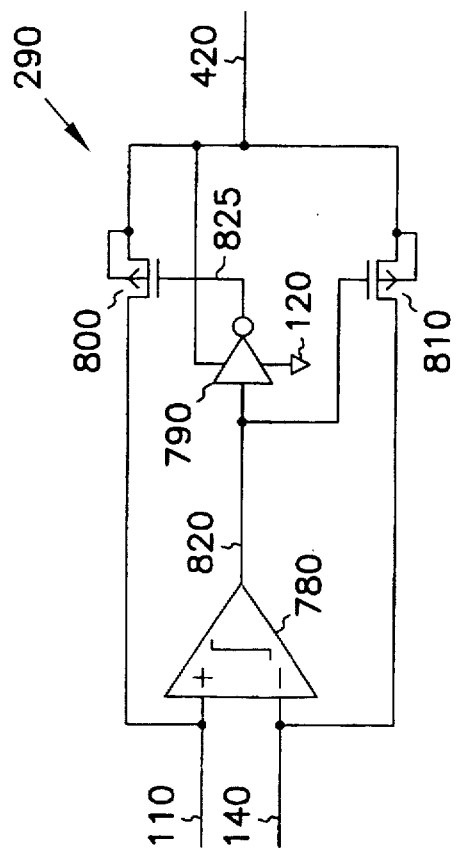
FIG. 8 is a schematic diagram illustrating the comparator/multiplexer of FIG. 4 in more detail.

FIG. 8 is a schematic diagram illustrating in more detail comparator/multiplexer 290 of FIG. 4 generating the voltage at most positive supply node 420. Comparator/multiplexer 290 comprises comparator 780, inverter 790, and PMOS FET first and second pass switches 800 and 810 respectively. Comparator 780 is coupled to first power supply node 110 at its positive input and is coupled to second power supply node 140 at its negative input. Comparator 780 provides an output at node 820 which is coupled to the input of inverter 790 and also coupled to the gate terminal of second pass switch 810. A power supply terminal of inverter 790 is coupled to most positive supply node 420. A ground terminal of inverter 790 is coupled to ground node 120. Inverter 790 provides an output coupled to the gate terminal of first pass switch 800 at node 825. First pass switch 800 has body and source terminals coupled to most positive supply node 420 and a drain terminal coupled to first power supply node 110. Second pass switch 810 has body and source terminals coupled to most positive supply node 420 and a drain terminal coupled to second power supply node 140.

When the voltage at first power supply node 110 is more positive than the voltage at second power supply node 140, the output of comparator 780 at node 820 is high and the output of inverter 790 at node 825 is low. In this state, first pass switch 800 is on, coupling first power supply node 110 to most positive supply node 420, and the second pass switch 810 is off. When second power supply node 140 is more positive than first power supply node 110, the output of comparator 780 at node 820 is low and the output of inverter 790 at node 825 is high. In this state, second pass switch 810 is on, coupling second power supply node 140 to most positive supply node 420, and the first pass switch 810 is off. Thus, comparator/multiplexer 290 couples the most positive of first and second power supply nodes 110 and 140 to most positive supply node 420.

Figure 9:
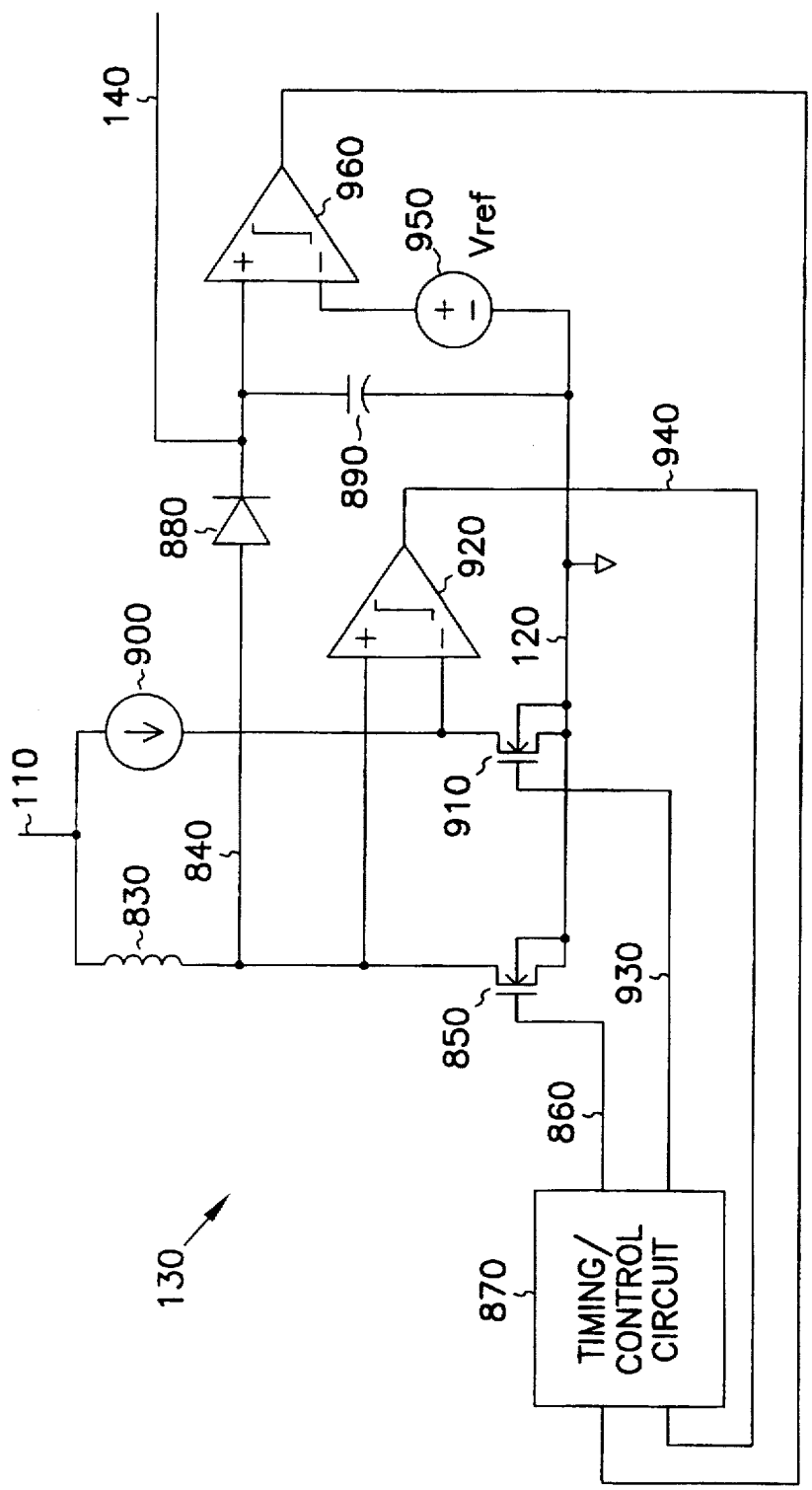
FIG. 9 is a schematic diagram illustrating the boost converter of FIG. 1 in more detail.

FIG. 9 is a schematic diagram illustrating boost converter 130 of FIG. 1 in more detail. Boost converter 130 is a switched-mode dc to dc converter having inductor 830 as a storage element. Inductor 830 is coupled to first power supply node 110 and to a drain terminal at node 840 of NMOS FET switch 850. Source and body terminals of NMOS FET switch 850 are coupled to ground node 120. A gate terminal of switch 850 receives a control signal at node 860 from timing/control circuit 870. In FIG. 9. rectifier diode 880 couples the drain terminal of switch 850 to a first terminal of filter capacitor 890 at second power supply node 140. Filter capacitor 890 has a second terminal coupled to ground node 120.

Boost converter 130 includes current reference 900, NMOS FET replicate switch 910, and comparator 920 which combine with timing/control circuit 870 to control charging of inductor 830 to a peak current value. Current reference 900 is coupled to a voltage bias source, such as first power supply node 110, and to a drain terminal of replicate switch 910. In another embodiment, the voltage bias source to which current reference 900 is the regulated output voltage at node 190. A gate terminal of replicate switch 910 receives a control signal at node 930 from timing/control circuit 870. Source and body terminals of replicate switch 910 are coupled to ground node 120. A positive input of comparator 920 is coupled to the drain terminal of switch 850. A negative input of comparator 920 is coupled to the drain terminal of switch 910. An output of comparator 920 is coupled to timing/control circuit 870 at node 940.

Boost converter 130 also includes reference voltage 950 and comparator 960 which combine with timing/control circuit 870 to provide stable voltage regulation at second power supply node 140. A negative terminal of reference voltage 950 is coupled to ground node 120. A positive terminal of reference voltage 950 is coupled to a negative input of comparator 960. A positive input of comparator 960 is coupled to the second power supply at node 140. An output of comparator 960 is provided to timing/control circuit 870.

Boost converter 130 operates in two phases. In a first phase, switch 850 is on, and inductor 830 is charged to a peak current value. The peak current value is reached when the voltage at the drain of switch 850 at node 840 is equal to the voltage at the drain of replicate switch 910 generated from current reference 900. Comparator 920 provides a binary logic high at its output at node 940 when the peak current value in inductor 830 is reached, causing timing/control circuit 870 to bring the control voltage at node 860 low, thereby turning off switch 850 and initiating a second phase. During this second phase when switch 850 is off, the drain voltage at node 840 increases, discharging inductor 830 through rectifier diode 880 and charging the filter capacitor 890 toward a more positive voltage at second power supply node 140. Timing/control circuit 870 then returns boost converter 130 to its first phase of operation. When the second power supply at node 140 exceeds a voltage determined by reference voltage 950, comparator 960 provides a binary logic low output to timing/control circuit 870, interrupting the switching of switch 850 and holding switch 850 in the second phase of boost converter 130 operation. When the voltage at second power supply node 140 is sufficiently discharged, timing/control circuit 870 resumes switching operation of switch 850.

Peak current control of switched mode dc to dc boost converters is discussed further in N. Mohan, T. M. Undeland, and W. P. Robbins, *Power Electronics: Converters, Applications and Design*, at 246-249 (John Wiley & Sons 1989), which is incorporated herein by reference. In the present invention, boost converter 130 receives the voltage at first power supply node 110 and generates and regulates the voltage at second power supply node 140. In one embodiment, the voltage at first power supply node 110 is generated by battery 100 having a characteristic internal impedance. During periods of large current draw from battery 100, the voltage between first power supply node 10 and ground node 120 may drop. Boost converter 130 provides a stable regulated voltage at second power supply node 140 over a wide range of voltage conditions at first power supply node 110.

In one embodiment, the present invention is part of an implantable cardiac rhythm management device such as an implantable defibrillator. In this embodiment, the voltage at first power supply node 110 is generated by battery 100. Battery 100 also supplies a load comprising a charging circuit for charging defibrillation output capacitors. The load is usually in a low power condition. However, the charging circuit presents a transient high power condition during charging of the defibrillation output capacitors causing a voltage drop at first power supply node 110.

As described above, regulator 180 is capable of being coupled to second power supply node 140 during the high power condition. In one embodiment, a microprocessor sequence which turns on the charging circuit also transitions the supply toggling signal at node 210 at approximately the same time. This decouples regulator 180 from first power supply node 110 and couples regulator 180 to second power supply node 110 which remains stable during the high power condition. As a result, regulator 180 is capable of providing a stable output voltage at the amplifier output terminal coupled to regulated output voltage node 190 during the high power condition. Thus, the present invention provides a stable regulated output voltage at node 190 from which to operate battery powered integrated circuits in spite of appreciable drop in battery terminal voltage during the high power condition.

Although specific embodiments have been illustrated and described herein for purposes of description of the preferred embodiment, it will be appreciated by those of ordinary skill in the art that a wide variety of alternate and/or equivalent implementations calculated to achieve the same purposes may be substituted for the specific embodiment shown and described without departing from the scope of the present invention. Those with skill in the electrical, computer, and telecommunications arts will readily appreciate that the present invention may be implemented in a very wide variety of embodiments. This application is intended to cover any adaptations or variations of the preferred embodiment discussed herein. Therefore, it is manifestly intended that this invention be limited only by the claims and the equivalents thereof.

What is claimed is:

1. A regulator for generating a regulated output voltage, the regulator comprising:

an amplifier circuit having a first amplifier power terminal;

a first switch coupled to the first amplifier power terminal for receiving a first power supply and coupling the first power supply to the first amplifier power terminal;

a second switch coupled to the first amplifier power terminal for receiving a second power supply and coupling the second power supply to the first amplifier power terminal; and a control circuit controlling the first and second switches such that the amplifier is capable of receiving power from the first and second power supplies.

2. The regulator of claim 1, wherein the amplifier further comprises noninverting and inverting amplifier input terminals, an amplifier output terminal, and a ground terminal.

3. The regulator of claim 2, further comprising:
   a first resistor coupled between the inverting amplifier input terminal and the amplifier output terminal;
   a second resistor coupled between the inverting amplifier input terminal and the ground terminal; and
   a reference voltage coupled to the noninverting amplifier input terminal.

4. The regulator of claim 3, wherein the amplifier further comprises a second amplifier power terminal.

5. The regulator of claim 4, further comprising:
   a third switch coupled to the second amplifier power terminal for receiving the first power supply and coupling the first power supply to the second amplifier power terminal; and
   a fourth switch coupled to the second amplifier power terminal for receiving the second power supply and coupling the second power supply to the second amplifier power terminal.

6. The regulator of claim 5, wherein the control circuit generates timing signals controlling the first, second, third, and fourth switches such that each of the first and second amplifier power terminals is not simultaneously coupled to both the first and second power supplies.

7. The regulator of claim 6, wherein the control circuit controls conductances of the third and fourth switches.

8. The regulator of claim 7, wherein the control circuit controls the conductances of the third and fourth switches as a function of a load current delivered at the amplifier output terminal.

9. The regulator of claim 4, further comprising a battery providing the first power supply.

10. The regulator of claim 4, further comprising a boost converter coupled to and receiving a voltage from the first power supply and providing the second power supply.

11. The regulator of claim 1, wherein the control circuit controls the first and second switches by generating timing signals.

12. The regulator of claim 11, wherein the timing signals control the first and second switches such that the first amplifier power terminal is not simultaneously coupled to both of the first and second power supplies.

13. An implantable cardiac rhythm management device comprising:
   a battery generating a first power supply;
   a boost converter receiving the first power supply and generating a second power supply; and
   a regulator receiving the first and second power supplies and generating an output voltage, wherein the regulator comprises:
      an amplifier having a first amplifier power terminal,
      a first switch coupling the first power supply to the first amplifier power terminal,
      a second switch coupling the second power supply to the first amplifier power terminal, and
      a control circuit coupled to a control terminal of each of the first and second switches for controlling the first and second switches such that the amplifier is capable of receiving power from both of the first and second power supplies.

14. The implantable cardiac rhythm management device of claim 13, wherein the amplifier further comprises noninverting and inverting amplifier input terminals, an amplifier output terminal, and a ground terminal.

15. The implantable cardiac rhythm management device of claim 14, further comprising:
   a first resistor coupled between the inverting amplifier input terminal and the amplifier output terminal;
   a second resistor coupled between the inverting amplifier input terminal and the ground terminal; and
   a reference voltage coupled to the noninverting amplifier input terminal.

16. The implantable cardiac rhythm management device of claim 15, wherein the amplifier further comprises a second amplifier power terminal.

17. The implantable cardiac rhythm management device of claim 16, further comprising:
   a third switch coupled to the second amplifier power terminal for receiving the first power supply and coupling the first power supply to the second amplifier power terminal; and
   a fourth switch coupled to the second amplifier power terminal for receiving the second power supply and coupling the second power supply to the second amplifier power terminal.

18. The implantable cardiac rhythm management device of claim 17, wherein the control circuit generates timing signals controlling the first, second, third, and fourth switches such that each of the first and second amplifier power terminals is not simultaneously coupled to both of the first and second power supplies.

19. The implantable cardiac rhythm management device of claim 17, further comprising controlled conductances of the third and fourth switches.

20. The implantable cardiac rhythm management device of claim 19, wherein the controlled conductances of the third and fourth switches are a function of a load current delivered at the amplifier output terminal.

21. The implantable cardiac rhythm management device of claim 16, further comprising a battery generating the first power supply.

22. The implantable cardiac rhythm management device of claim 21, further comprising a boost converter coupled to and receiving a voltage from the first power supply and the boost converter generating the second power supply.

23. The implantable cardiac rhythm management device of claim 13, wherein the control circuit generates timing signals for controlling the first and second switches.

24. The implantable cardiac rhythm management device of claim 23, wherein the timing signals control the first and second switches such that first amplifier power terminal is not simultaneously coupled to both of the first and second power supplies.

25. The implantable cardiac rhythm management device of claim 13, wherein the control circuit prevents the amplifier from simultaneously receiving power from both of the first and second power supplies.

* * * * *